United States Patent
Niemela et al.

(10) Patent No.: US 9,927,372 B2
(45) Date of Patent: Mar. 27, 2018

(54) APPARATUS AND METHOD FOR INSPECTING SEALS OF ITEMS

(71) Applicant: FOCALSPEC OY, Oulu (FI)

(72) Inventors: Karri Niemela, Oulu (FI); Heimo Keranen, Oulu (FI)

(73) Assignee: FOCALSPEC OY, Oulu (FI)

( * ) Notice: Subject to any disclaimer, the term of this patent is extended or adjusted under 35 U.S.C. 154(b) by 278 days.

(21) Appl. No.: 14/441,856

(22) PCT Filed: Nov. 12, 2013

(86) PCT No.: PCT/EP2013/003406
§ 371 (c)(1),
(2) Date: May 11, 2015

(87) PCT Pub. No.: WO2014/075792
PCT Pub. Date: May 22, 2014

(65) Prior Publication Data
US 2015/0241360 A1     Aug. 27, 2015

(30) Foreign Application Priority Data

Nov. 13, 2012  (GB) .................................... 1220397.2

(51) Int. Cl.
*G01N 21/90* (2006.01)
*G01N 21/95* (2006.01)

(52) U.S. Cl.
CPC ......... *G01N 21/9054* (2013.01); *G01N 21/95* (2013.01); *G01N 21/9508* (2013.01);
(Continued)

(58) Field of Classification Search
CPC ............... G01N 21/95; G01N 21/9054; G01N 21/9508; G01B 2210/50
See application file for complete search history.

(56) References Cited

U.S. PATENT DOCUMENTS 6,674,572 B1 * 1/2004 Scheruebl .......... G02B 21/0024
                                                356/237.5
6,917,421 B1 * 7/2005 Wihl .................. G01B 11/0608
                                                356/237.5
(Continued)

FOREIGN PATENT DOCUMENTS

EP      1304560 A1    4/2003
GB      2453535 A     4/2009
(Continued)

OTHER PUBLICATIONS

International Search Report and Written Opinion of International Searching Authority for PCT/EP2013/003406 dated Mar. 13, 2014 (10 pages).

*Primary Examiner* — Hina F Ayub
*Assistant Examiner* — Amanda Merlino
(74) *Attorney, Agent, or Firm* — Ziegler IP Law Group, LLC

(57) ABSTRACT

A measuring apparatus is provided for inspecting a seal of an item. The measuring apparatus includes a radiation source for providing radiation for illuminating the seal of the item, a detector for receiving radiation from the item for generating a corresponding detected signal, and a processing arrangement for processing the detected signal to generate an output signal indicative of a state of the seal. The radiation source is arranged to focus the radiation into a plurality of focal points at the seal of the item, wherein the focal points are mutually spatially spaced apart. Moreover, the detector is arranged to image one or more of the focal points and to be selectively sensitive to an intensity of radiation received from the one or more focal points to generate a detected signal.

18 Claims, 17 Drawing Sheets

(52) U.S. Cl.
CPC ............... *G01N 2201/061* (2013.01); *G01N 2201/0683* (2013.01)

(56) References Cited

U.S. PATENT DOCUMENTS

| | | |
|---|---|---|
| 7,142,707 B2 | 11/2006 | Abdollahi |
| 2010/0118138 A1 | 5/2010 | Djachiachvili |
| 2010/0296107 A1 | 11/2010 | Keranen |

FOREIGN PATENT DOCUMENTS

| | | |
|---|---|---|
| WO | 2005/114155 A1 | 12/2005 |
| WO | 2010/052431 A1 | 5/2010 |

* cited by examiner

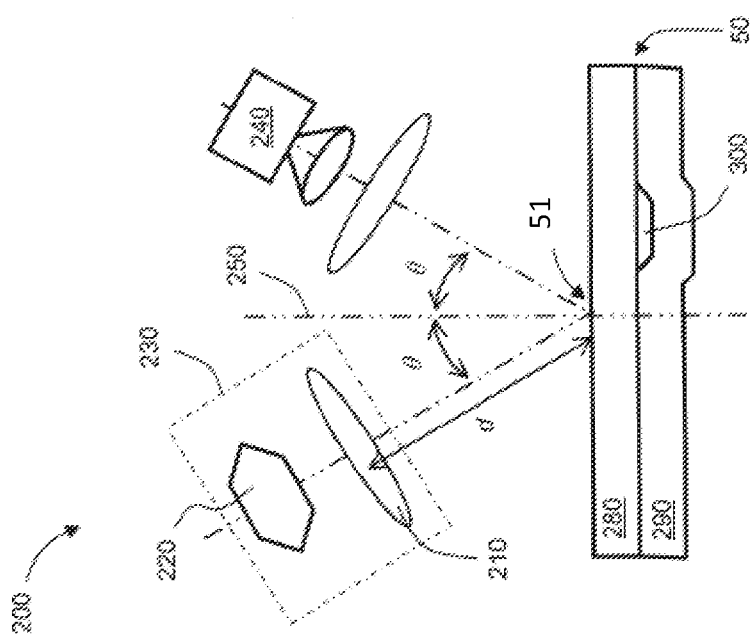

APPARATUS AND METHOD FOR INSPECTING SEALS OF ITEMS

FIELD OF THE INVENTION

The present invention relates to apparatus for inspecting seals of items, for example peripheral seals of packages wherein the seals are intended to provide a sterile environment within the packages. Moreover, the present invention relates to method of inspecting seals of items, for example to methods of inspecting seals of packages wherein the seals are intended to provide a hermetic or antiseptic environment within the packages. Furthermore, the present invention relates to software products recorded on machine-readable data storage media, wherein the software products are executable upon computing hardware for implementing aforesaid methods.

BACKGROUND OF THE INVENTION

As illustrated in FIG. 1, it has become contemporary practice to package products 10, for example foodstuffs, medicines, disposal medical devices, in packages indicated by 20, wherein each package includes a base 30, optionally with a recess, to receive the product 10, and a cover 40 which is sealed via a seal 50 to the base 30 to enclose the product 10. For certain categories of product 10, for example medical products which must remain in a sterile environment prior to being used, the seal 50 is beneficially airtight so that the product 10 is retained in a hermetically-sealed or antiseptic environment. Moreover, the seal 50 is conventionally implemented in several different manners, depending upon requirements, for example using adhesives, by heating, by welding and so forth. The seal 50 is required to be sufficiently mechanically strong to withstand handling of the packaging 20. Contemporary examples of packaging are manufactured, for example, by a DuPont, for example in association with its registered trade mark Tyvek® as reported at a web-site:
http://www2.dupont.com/Medical_Packaging/en_US/products/index.html It is important that the seal 50 is reliable, for example potentially over a period of many years when packages are in storage and are awaiting to be deployed, for example as emergency medical supplies to be deployed in disaster zones around the World. A fault or failure of the seal 50 in a context of medical products stored in a package 20 can potentially be fatal, because a broken seal may potentially result in contamination, for example bacteria, mould, entering into the package 20. Moreover, in relation to food products, food stored in the package 20 can become rotten or spoiled, rendering it dangerous for consumption, if its seal 50 is not properly formed.

In a packaging line, along which products 10 are placed and sealed into corresponding packages 20, it is well known to employ inspection apparatus including one or more cameras linked to computing hardware executing image processing software to view the packages 20 after their seals 50 have been formed, wherein the computing hardware executes one or more algorithms to process images of the seals 50 for determining whether or not the seals 50 have been correctly formed, for example to be devoid of bubbles, occlusions, debris, moisture and such like. Such known inspection apparatus is described in published patent applications, for example:

| Document | Detail |
| --- | --- |
| JP4523474B2 | "Defect inspection device and PTP packaging machine", Applicant CKD |
| U.S. Pat. No. 7,142,707 | "Automated inspection of packaging materials for package integrity", Applicant Northrop Grumman |

Common and conventional seal Integrity testing and inspection procedure used widely in medical industry is described in the ASTM Standard <<Standard Test Methods for Detecting Seal leaks in Porous Medical Packaging by Dye Penetration>>, Designation: F1929-98 (Reapproved 2004). This procedure is based on dye penetration: Dye is injected with a dispenser to inside the package and the seal is then inspected visually if there are channels etc. visible in the seal area. The disadvantages of this method are: It is very time consuming, and it destroys the package.

A problem encountered, when employing image processing of packages 20 for determining integrity of their seals 50, is that computer-automated inspection of the seals 50 is time-consuming and requires considerable costly computing capacity for its implementation. Additionally, camera based imaging systems with conventional illumination and imaging solutions yield very poor contrast for the package seal area. Heat seals have very poor contrast and it is difficult to build a reliable image processing algorithm to investigate seal integrity. For a manufacturing environment where the packages 20, with their products 10 enclosed, are produced in great numbers, employing aforesaid computer-automated inspection of the seals 50 causes an undesirable limit on feasible production rate of the packages 20, namely causes a "bottle neck" in a packaging production environment. Employing numerous inspection apparatus in parallel to resolve such a "bottle-neck" represents an expensive solution. It has thus become established conventional practice to sample packages 20 from a packaging line at intervals and then inspect the sample packages 20 for quality of their seals 50, assuming that the sample packages 20 are representative of all packages 20 being processed along the packaging line.

Alternative approaches to inspect seals 50 have been proposed. For example, in a published United States patent application no. US2012/0206710 ("Measuring instrument and method for determination of the properties of an item and its surface", Applicant Tutkimuskeskus VTT), there is described a measurement device as indicated generally by 100 in FIG. 2. The measurement device 100 is operable to determine characteristics of an object's surface 110 by means of optical radiation, wherein the measurement device 100 comprises an optical radiation source 120 which is operable to illuminate the surface 110 and a detector 130 which is operable to receive radiation which is reflected from the surface 110. Moreover, the measurement device 100 includes an emitted optical radiation unit 140 which is operable to split optical radiation emitted by the optical radiation source 120 into separate wavelengths components and to direct the separate wavelength components to the surface 110 in a direction which is non-orthogonal to a plane of the surface 110, for example at an inclined angle as illustrated, so that shortest and longest wavelength components are focused on different portions and at different heights on the surface 110. Furthermore, the measurement device 100 includes a reflected optical radiation processing unit 150, which is operable to receive reflected optical radiation from the surface 110, at least in a direction of specular reflection, and provide the received radiation to the aforesaid detector 130. The measurement device 100 further includes computing hardware 160 for analyzing an electrical signal generated by the detector 130 in response to receiving reflected radiation thereat.

The computing hardware 160 is operable to determine a surface gloss measurement of the surface 110 and/or thickness measurements of the surface 110, based on the relative intensity of the wavelength components reflected from various points on the surface 110.

A problem encountered in practice is that aforesaid measurement devices 100, for example as illustrated in FIG. 2, are capable of being used to make measurements of surfaces 110, but are not ideal for checking seals 50 of packages 20, for example for detecting occluded air bubbles, debris and similar in manufacturing line environment.

SUMMARY OF THE INVENTION

The present invention seeks to provide a measuring apparatus which is capable of inspecting seals more rapidly, whilst employing less computing resources.

The present invention also seeks to provide a method of using a measuring apparatus to inspect seals more rapidly, whilst employing less computing resources.

According to a first aspect of the invention, there is provided a measuring apparatus as claimed in appended claim 1: there is provided a measuring apparatus for inspecting a seal of an item, wherein the measuring apparatus includes a radiation source for providing radiation for illuminating the seal of the item, a detector for receiving radiation from the item for generating a corresponding detected signal, and a processing arrangement for processing the detected signal to generate an output signal indicative of a state of the seal, characterized in that:
(a) the radiation source is arranged to focus the radiation into a plurality of focal points at the seal of the item, and wherein the focal points are mutually spatially spaced apart;
(b) the detector is arranged to image one or more of the focal points and to be selectively sensitive to an intensity of radiation received from the one or more focal points to generate a detected signal; and
(c) a processing arrangement for receiving the detected signal and for processing the detected signal to generate the output signal indicative of the state of the seal.

The invention is of advantage that the plurality of focal points at the seal of the item, wherein the focal points are mutually spatially spaced apart, and wherein signal from each focal point enables one or more interfaces of the seal to be inspected rapidly for determining their state, enables more rapid inspection of the seal to be achieved.

Optionally, one or more focal points are generated in a direction which intersects the plane of the seal when being inspected.

Optionally, the measuring apparatus is arranged to inspect packages in which products are hermetically sealed.

Optionally, in the measuring apparatus, the radiation source employs chromatic dispersion occurring in one or more optical components for generating the plurality of focal points.

Optionally, in the measuring apparatus, the focal points are generated as a function of depth (h) in a direction which intersects the plane of the seal when being inspected.

Optionally, in the measuring apparatus, the detector includes a spectrometer and an image camera for generating the detected signal.

Optionally, in the measuring apparatus, the detector includes one or more radiation polarizing elements for increasing signal contrast in the detected signal arising from one or more defects being present in the seal.

Optionally, in the measuring apparatus, the processing arrangement is operable to detect one or more radiation peaks present in the detected signal as a function of either radiation wavelength ($\lambda$) and/or as function of depth (h) from the top of the measured seal, to determine a magnitude of the one or more radiation peaks, and to determine from a relative ratio of the magnitude of the one or more radiation peaks the state of the seal. More optionally, in the measuring apparatus, the state of the seal determined by the processing arrangement includes at least one of: bubbles present at an interface of the seal, debris present at an interface of the seal.

Optionally, the measuring apparatus includes an arrangement for moving the item relative to the plurality of focal points, for enabling the measuring apparatus to map a tomography of an interface between layers forming the seal, based on the relative refractive index of the layers to the radiation received from the radiation source.

According to a second aspect of the invention, there is provided a method of using a measuring apparatus to inspect a seal of an item, wherein the measuring apparatus includes a radiation source for providing radiation for illuminating the seal of the item, a detector for receiving radiation from the item for generating a corresponding detected signal, and a processing arrangement for processing the detected signal to generate an output signal indicative of a state of the seal, characterized in that the method includes:
(a) employing the radiation source to focus the radiation into a plurality of focal points at the seal of the item, wherein the focal points are mutually spatially spaced apart, and wherein each focal point has a corresponding radiation wavelength;
(b) using the detector to image one or more of the focal points and to be selectively sensitive to an intensity of radiation received from the one or more focal points as a function of radiation wavelength to generate a detected signal; and
(c) receiving at a processing arrangement the detected signal and processing the detected signal to generate the output signal indicative of the state of the seal.

Optionally, the method includes employing in the radiation source chromatic dispersion occurring in one or more optical components, for example one or more lenses, for generating the plurality of focal points.

Optionally, the method includes generating the focal points as a function of either radiation wavelength ($\lambda$) and/or as a function of depth (h) in a direction which is orthogonal to a plane or intercepts the plane of the seal when being inspected.

Optionally, the method includes employing in the detector a spectrometer and an image camera for generating the detected signal.

Optionally, the method includes employing in the detector one or more radiation polarizing elements for increasing signal contrast in the detected signal arising from one or more defects being present in the seal.

Optionally, the method includes using the processing arrangement to detect one or more radiation peaks present in the detected signal as a function of either radiation wavelength ($\lambda$) and/or as a function of depth (h), to determine a magnitude of the one or more radiation peaks, and to determine the state of the seal from a relative ratio of the magnitude of the one or more radiation peaks. More optionally, in the method, the state of the seal determined by the processing arrangement includes at least one of: bubbles present at an interface of the seal, debris present at an interface of the seal.

Optionally, the method includes arranging for the measuring apparatus to include an arrangement for moving the item relative to the plurality of focal points, for enabling the measuring apparatus to map a tomography of an interface between layers forming the seal, wherein the layers have mutually different refractive indices to the radiation received from the radiation source.

According to a third aspect of the invention, there is provided a software product recorded on machine-readable data storage media, where the software product is executable upon computing hardware for executing a method pursuant to the second aspect of the invention.

It will be appreciated that features of the invention are susceptible to being combined in various combinations without departing from the scope of the invention as defined by the appended claims.

DESCRIPTION OF THE DIAGRAMS

Embodiments of the present invention will now be described, by way of example only, with reference to the following diagrams wherein:

FIG. 4A, 4B, 4C are schematic representations of measuring apparatus pursuant to embodiments of the present invention;

Figure 1:
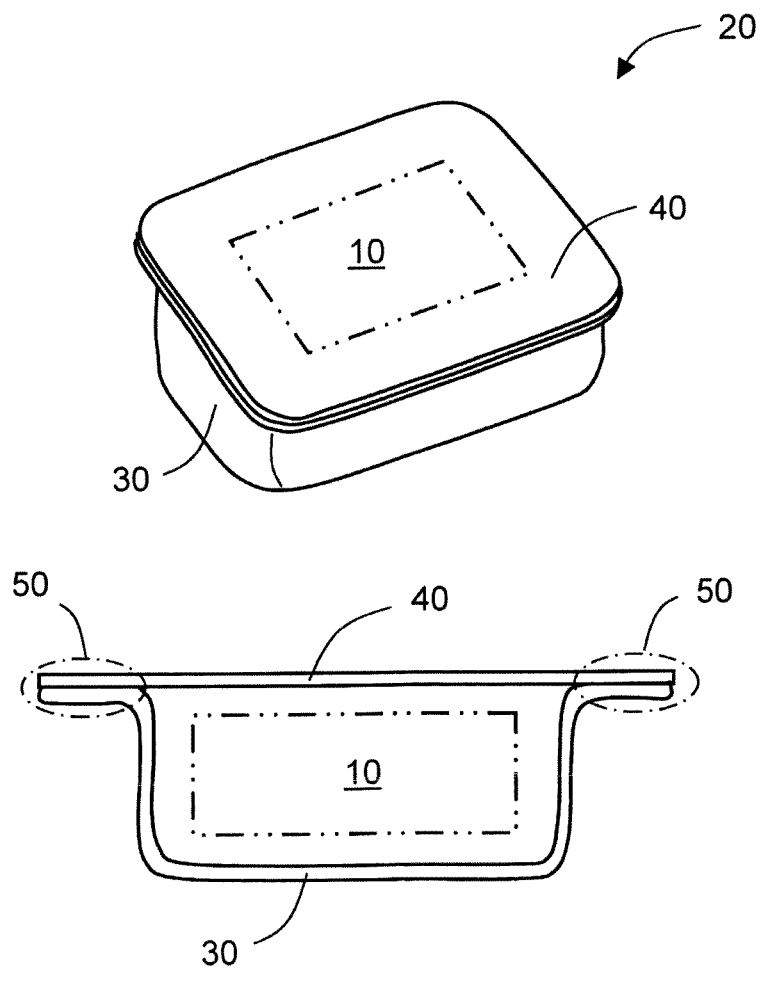
FIG. 1 is a schematic illustration of a package for enclosing a product.
Figure 2:
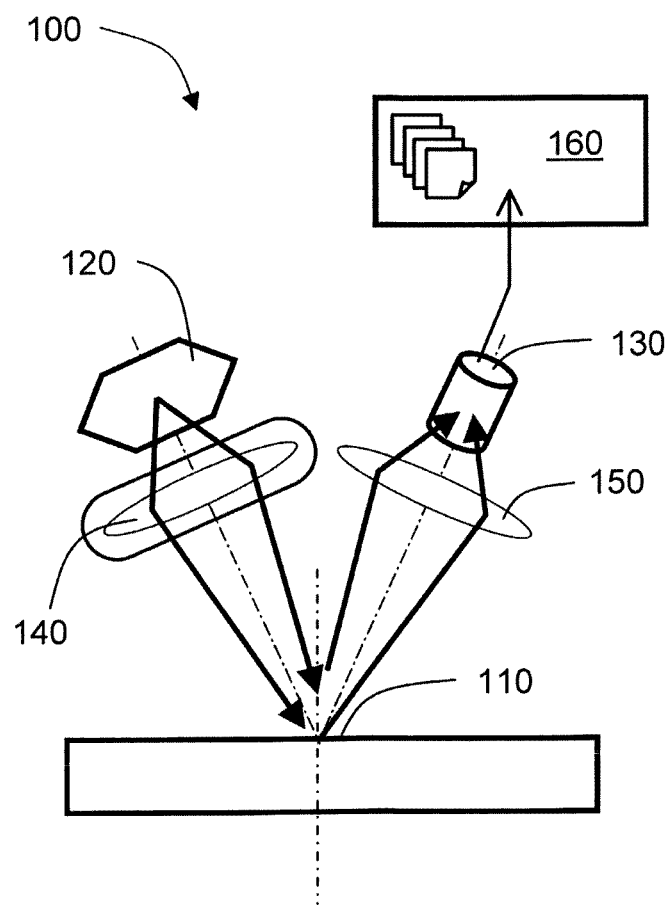
FIG. 2 is a schematic illustration of a known measuring device for measuring characteristics of a surface by employing mutually different radiation wavelength components.

In the accompanying diagrams, an underlined number is employed to represent an item over which the underlined number is positioned or an item to which the underlined number is adjacent. A non-underlined number relates to an item identified by a line linking the non-underlined number to the item. When a number is non-underlined and accompanied by an associated arrow, the non-underlined number is used to identify a general item at which the arrow is pointing.

DESCRIPTION OF EMBODIMENTS OF THE INVENTION

In overview, the present invention is concerned with apparatus for inspecting seals of items, for example at peripheral edges of packages for providing a sterile environment within the packages. The apparatus is operable to utilize a phenomenon wherein chromatic dispersion is a feature of an optical component, or a configuration of optical components, to focus radiation of different colours, namely different radiation wavelengths, to different convergence points, namely to spatially different focal points. Chromatic dispersion arises because the optical component, or the configuration of optical components, is fabricated from an optical material whose refractive index decreases as the wavelength of light transmitted therethrough decreases. For example, referring to FIG. 4A, there is shown a measuring apparatus 200 including a lens arrangement denoted by 210, wherein a distance d from the lens arrangement 210 to a surface 51 of a seal 50 to be interrogated defines which colour component is in focus at the surface 51 of the seal 50. Such a characteristic can be used to perform high-speed inspection of seals as will be described in detail later. In FIG. 4A, the lens arrangement 210 configured in combination with a light source 220 are operable to function as a polychromic light source denoted collectively by 230. The measuring apparatus 200 further includes a black-white line-scan camera 240 with associated optical components for measuring an intensity of reflected radiation components as a function of radiation wavelength received at the camera 240. The camera 240 and polychromatic light source 230 are arranged to subtend a non-orthogonal angle □ relative to an orthogonal axis 250 to a plane of the surface 51 of the seal 50.

Figure 4B:
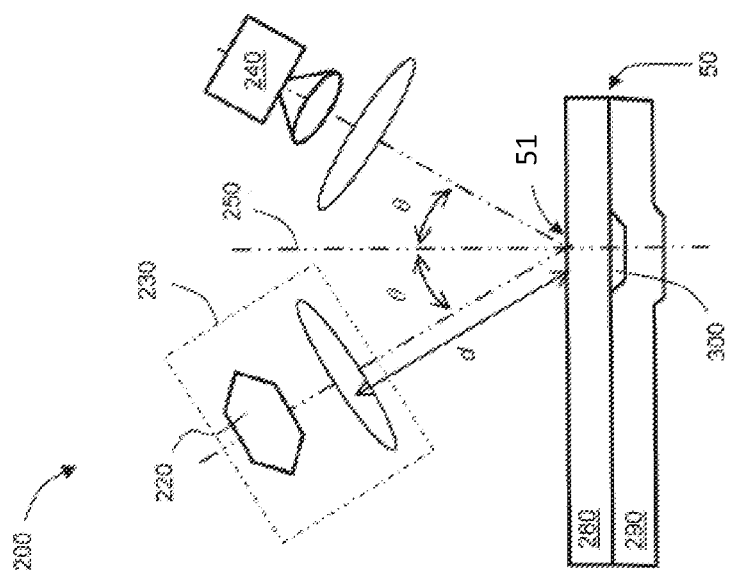
Figure 5A:
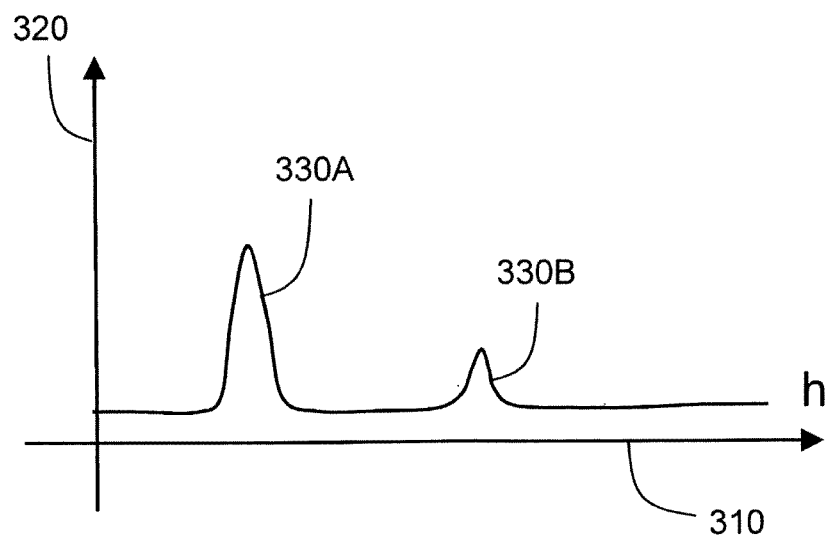
FIG. 5A, 5B, 5C are example reflected radiation signals generated by the measuring apparatus of FIG. 3A, FIG. 3B, FIG. 3C respectively.

The surface 51 is represented in FIG. 4A as a plastics material layer 280 formed onto a base layer 290. Occasionally, a defect 300 may arise at an interface between the plastics material layer 280 and the base layer 290; above the plastics material layer 280 is a region of air. The measuring apparatus 200 is operable to measure substantially along the orthogonal axis 250 where it intersects with the layers 280, 290. Radiation provided from the light source 230 is reflected at an interface between the plastics material layer 280 and air, as well as from the interface between the plastics material layer 280 and the base layer 290, to be received at the black-white line scan camera 240 to provide a scanned signal as illustrated in FIG. 5A. In FIG. 5A, an abscissa axis 310 denotes a depth (h) into the seal 50 which is also a function of radiation wavelength, and an ordinate axis 320 denotes intensity of reflected radiation; the measurement apparatus 200 results in two peaks 330A, 330B being measured when the defect 300 is remote from the orthogonal axis 250 as illustrated in FIG. 4A. However, as illustrated in FIG. 4B, when the seal 50 is moved laterally relative to the orthogonal axis 250, such that the defect 300 lies substantially along the orthogonal axis 250, there arise three interfaces at which reflection of radiation can occur, namely:

(i) at the interface between the plastics material layer 280 an air thereabove;

(ii) at an interface between the plastics material layer 280 and air included within the defect 300; and (iii) at an interface between the air included in the defect 300 and the base layer 290.

Figure 5B:
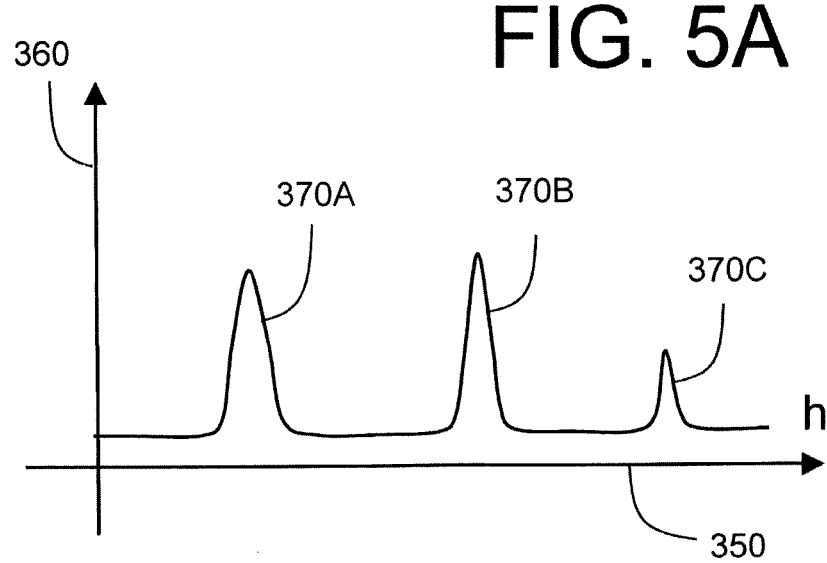

Reflected radiation from the seal 50 in FIG. 4B is reflected to the black-white line scan camera 240 to provide a scanned signal as illustrated in FIG. 5B. In FIG. 5B, an abscissa axis 350 denotes a depth (h) into the seal 50 which is a function of radiation wavelength, and an ordinate axis 360 denotes intensity of reflected radiation; the measurement apparatus 200 results in three peaks 370A, 370B, 370C being measured when the defect 300 is spatially coincident with the orthogonal axis 250 as illustrated in FIG. 4B.

Figure 4C:
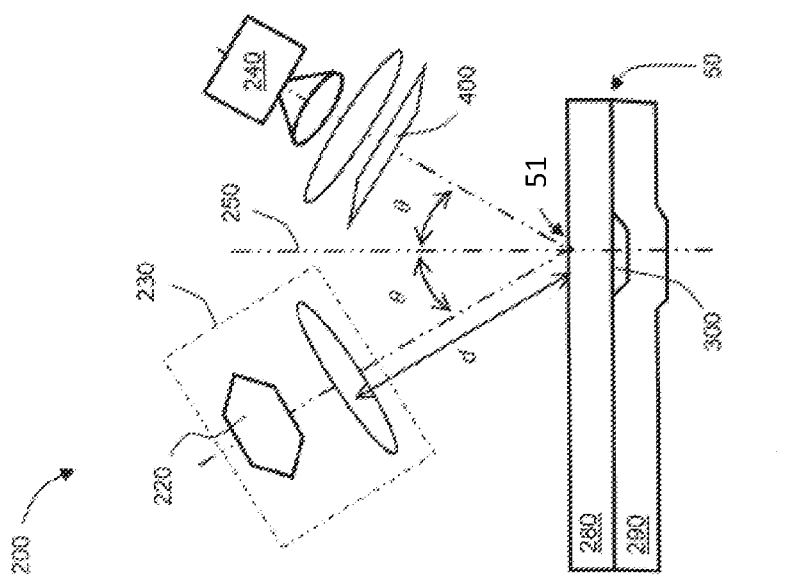
Figure 5C:
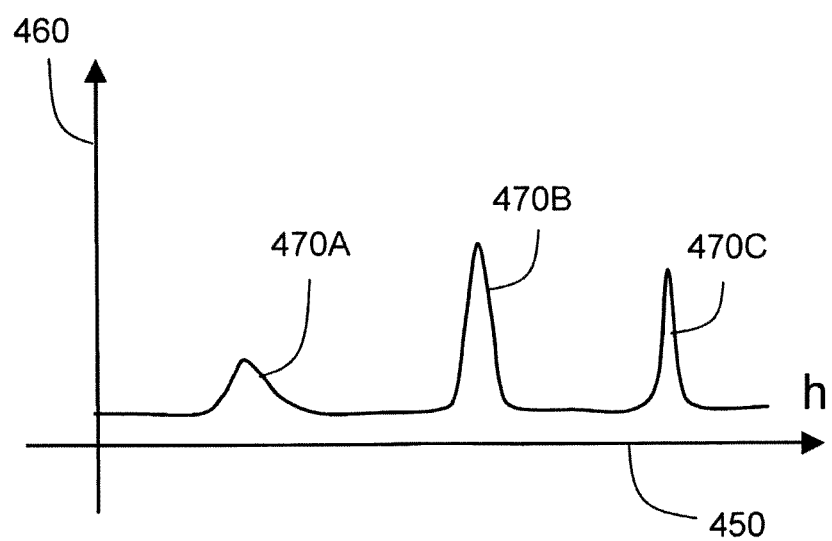

Optionally, as illustrated in FIG. 4C, a polarizer component 400, or a combination of polarizer components, is included between the seal 50 and the black-white line scan camera 240 to remove the peak 370A arising from the interface between the plastics material layer 280 and air thereabove, thereby providing the measuring apparatus 200 with a contrast-enhanced measurement of the defect 300 when substantially spatially coincident with the orthogonal axis 250, wherein the contract-enhanced measurement is illustrated in FIG. 5C. In FIG. 5C, an abscissa axis 450 denotes a depth (h) into the seal 50 which is function of radiation wavelength, and an ordinate axis 460 denotes intensity of reflected radiation; the measurement apparatus 200 results in three peaks 470A, 470B, 470C being measured when the defect 300 is spatially coincident with the orthogonal axis 250 as illustrated in FIG. 4C. In comparison to FIG. 5B, the peak 470A is much smaller amplitude than the peak 370A, thus enabling the peaks 470B, 470C to be more accurately and reliably measured.

Implementations of the measuring apparatus 200 as illustrated in FIG. 4A to FIG. 4C can be used measure thicknesses of optical-radiation transmissive layers, as well as measuring an occurrence of defects, for example impurities and/or air bubbles. Moreover, the measuring apparatus 200 can also be used be measured a width of the seal 50 in a plane of the surface 51. Such measurements can be employed for determining a quality of the seal 50. On account of the measuring apparatus 200 measuring peaks in signals provided from the black-white line scan camera 240, for example using computing hardware coupled to the camera 240, there is thereby avoided a need to perform image processing as arises in known measuring apparatus, thereby enabling a higher seal-inspection rate to be achieved. Reflected radiation received at the camera 240, and corresponding signals generated therefrom for analysis in the computing hardware, are different for a perfect seam 50 in comparison to the seam 50 including defects such as bubbles and debris.

Thus, in overview, the measuring apparatus 200 is operable to employ chromatically dispersed optical techniques, wherein focal points of wavelength components derived from the polychromic light source 230 are arranged to occur at different depths (h) within the seam 50, and the black-white line scan camera 240 is operable to image the focal points as a function of wavelength and therefrom identify the different depths in the seal 50 by apply appropriate data processing, for example based upon a look-up table and/or rule-based algorithm.

An example embodiment of the measuring apparatus 200 will now be described with reference to FIG. 6. The FIG. 6, the measuring apparatus 200 includes a mount 500 onto which is mounted a polychromic light source implemented using a white light emitting diode (LED) 510 having a small spatial size, and a lens arrangement 520 to receive light from the LED 510. The lens arrangement 520 is operable to cause wavelength-dependent dispersion of light emitted from the LED 510 in a direction off-axis from a principal axis of the lens arrangement 520. Moreover, the measuring apparatus 500 includes a wavelength-discriminating sensor including a spectrograph 530 and a camera 540. The polychromic light source and the wavelength-discriminating sensor are arranged to subtend an angle θ relative to a plane of a seam 50 to be inspected using the measuring apparatus 200.

Operation of the measuring apparatus 200 of FIG. 6 will next be described with reference to FIG. 7. In FIG. 7, a cross-sectional view of the seal 50 is shown, wherein a region of air is denoted by 600, a plastics material base layer is denoted by 610, and a cover layer is denoted by 620, wherein the seal 50 is formed at an interface between the layers 610, 620; optionally, the base layer 610 is fabricated from paper or Tyvek and consequently optically opaque. Various defects, like bubbles of air 630, occur at an interface between the plastics material layer 610 and the cover layer 620 which can potentially cause a degradation in a quality of the seal 50. Components of different wavelength generated by the polychromatic light source are denoted by 650A, 650B, 650C and are brought to corresponding focal points at the interfaces as shown in FIG. 7. In a perfect seam 50, the components 650B, 650C would be identical, but mutually differ as the defects 630 become more significant. The wavelength components which are spatially focussed at the interfaces and received at the wavelength-discriminating sensor give rise to distinct measurement peaks as aforementioned, which move around in frequency as illustrated in FIG. 5A, FIG. 5B, FIG. 5C as thickness of the layer 610 varies and the defects 630 are present at the interface between the layers 610, 620. Amplitude of the measurement peaks as function of movement of measured object provides an indication of the size and frequency of spatial occurrence of the defects 630. Thus, in case of a problem between the layers 610, 620, intensity of the measurement peaks is beneficially employed to identify the problem.

Figure 6:
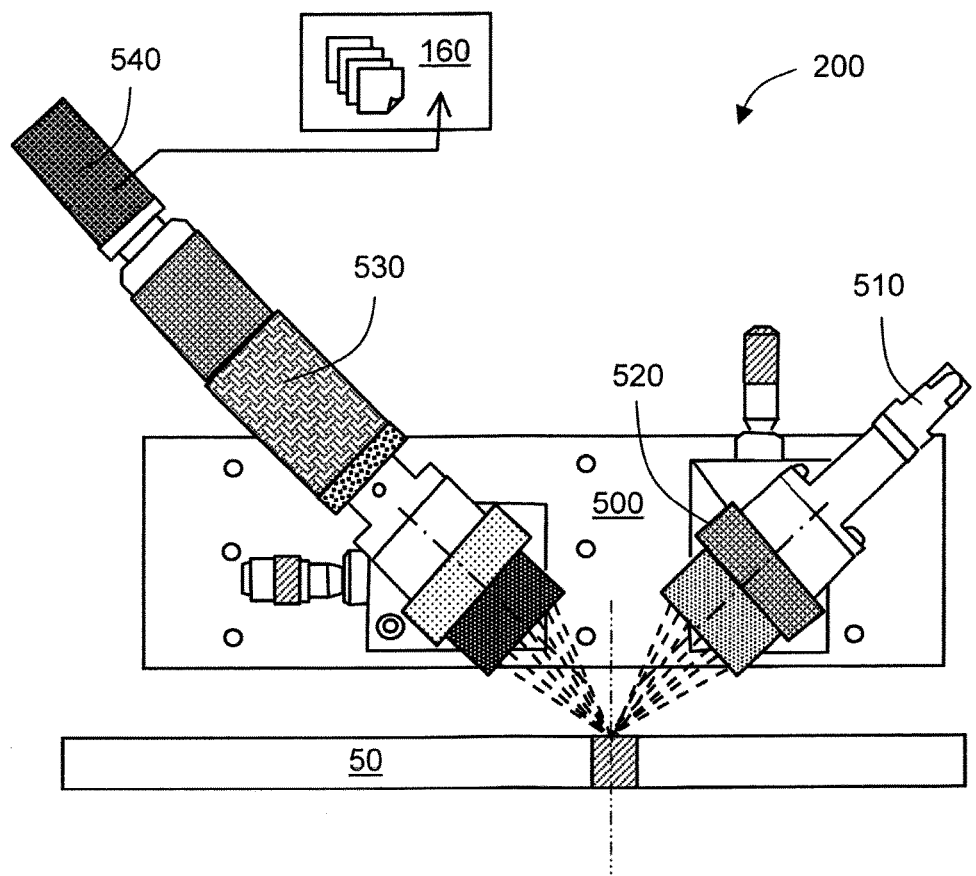
FIG. 6 is an illustration of an example embodiment of the present invention.
Figure 7:
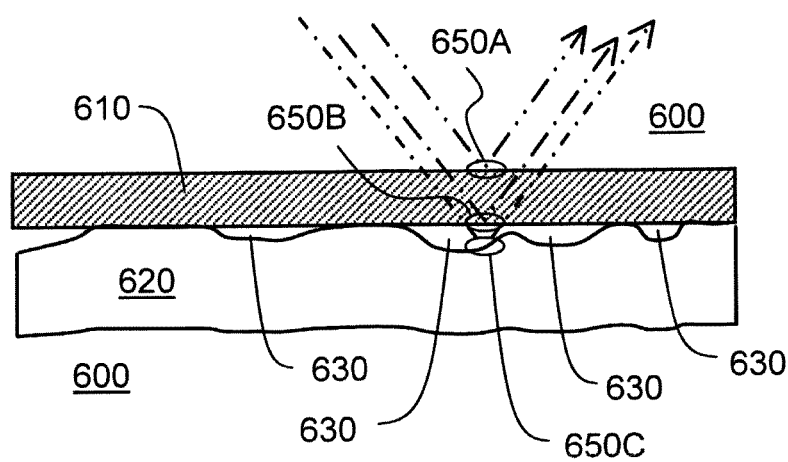
FIG. 7 is an illustration of wavelength components being reflected from various layers occurring within a seam of a package.
Figure 8A:
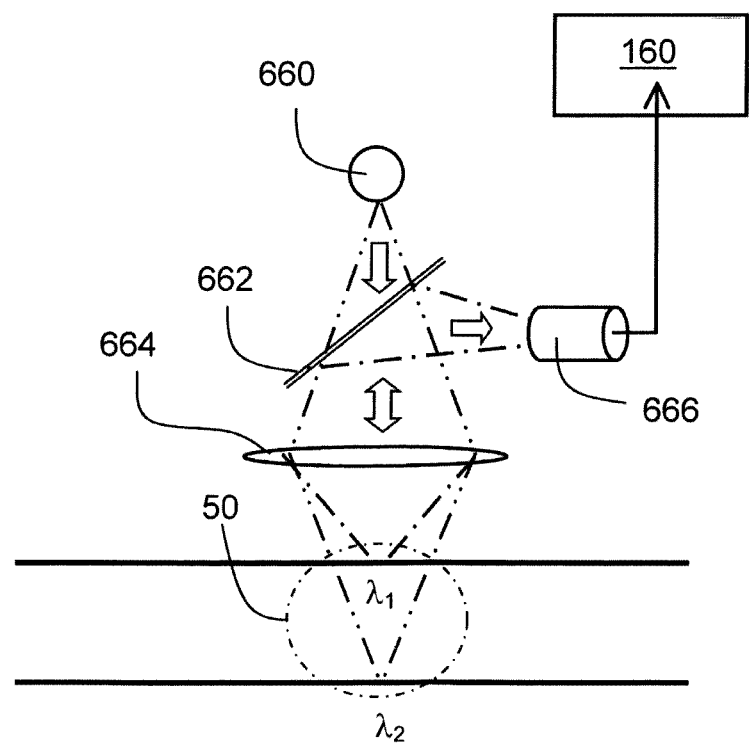
FIG. 8A, 8B, 8C, 8D are alternative optical configurations which are optionally employed when implementing the measuring apparatus of FIG. 6.
Figure 8B:
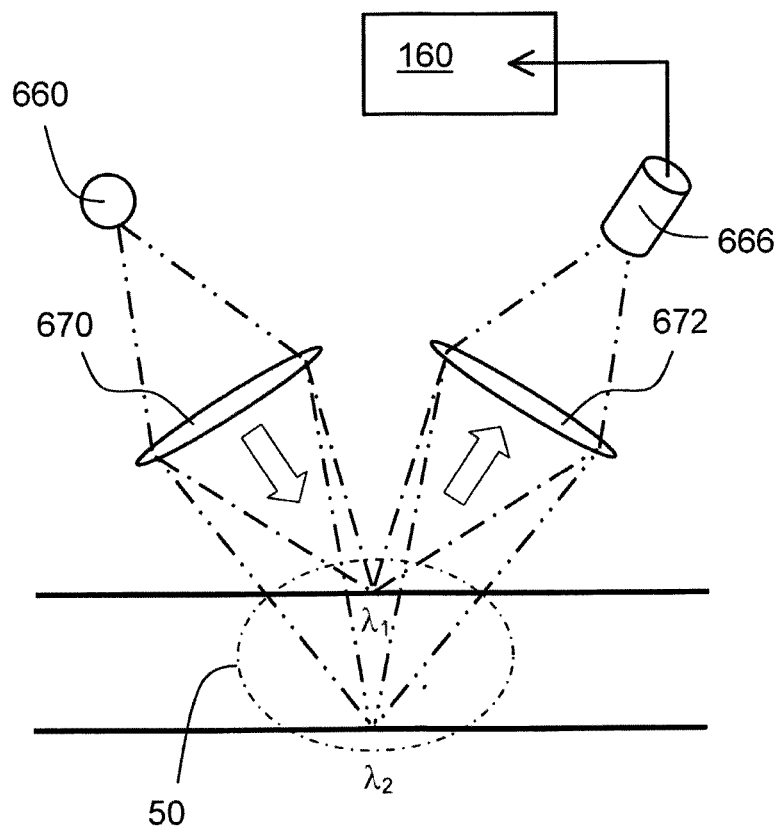
Figure 8C:
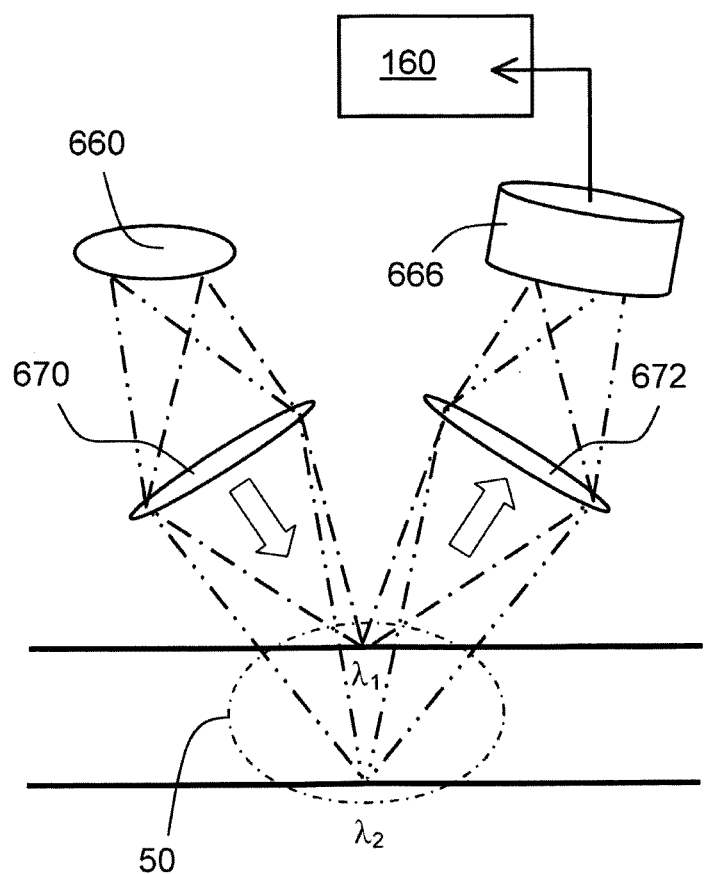
Figure 8D:
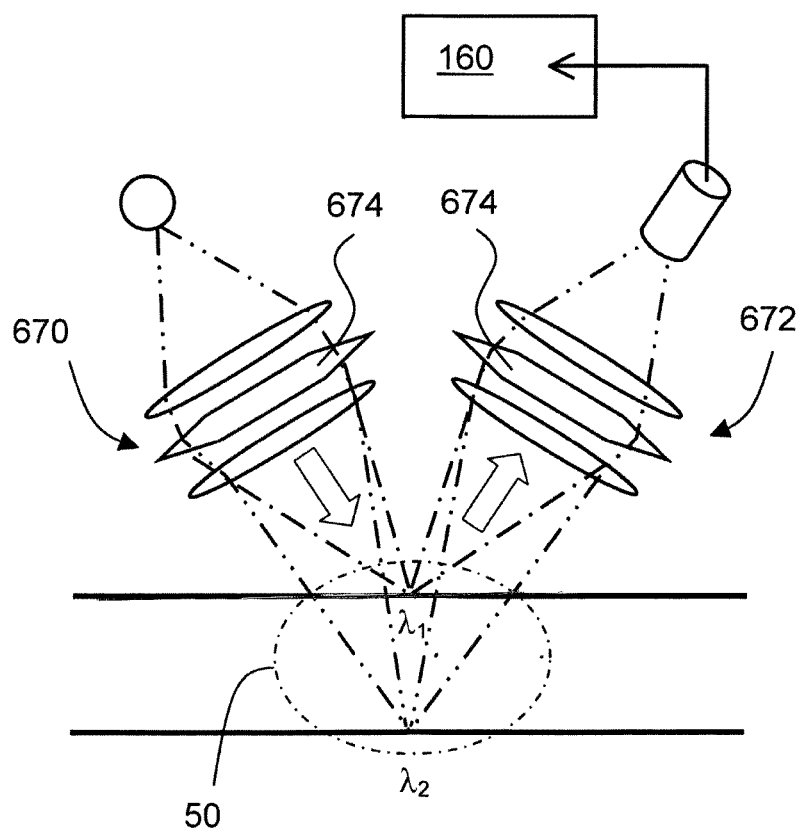

Although an example of the measuring apparatus 200 is provided in FIG. 6, alternative optical arrangements for implementing the measuring apparatus 200 are feasible, for example as illustrated in FIG. 8A to FIG. 8D. In FIG. 8A, single axis chromatic wavelength-dependent dispersion is employed in the measuring apparatus 200 for forming different foci for different wavelength radiation as a function of depth into the layers 610, 620; optionally, an optical source 660 and an optical receiver 666 of the measuring apparatus 200 employ one or more optical components 664 which are mutually common thereto, and a beam splitter 662 to separate interrogating radiation for illuminating the seal 50 and reflected radiation from the seal 50. In FIG. 8B and FIG. 8C, the measuring apparatus 200 employs two lens arrangements 670, 672 for its optical source 660 and optical receiver 666 respectively, wherein the two lens arrangements 670, 672 exhibit chromatic aberration for forming and imaging different foci for different radiation wavelengths; in FIG. 8C, focal depths arise at laterally different positions. As aforementioned, the measuring apparatus 200 is operable to generate a plurality of mutually different foci as a function of radiation wavelength, and the apparatus 200 is operable to sense radiation reflected at interfaces between layers exhibiting mutually different refractive indexes, such that measuring apparatus 200 is operable to determine spatial positions of the interfaces by analysing a wavelength of radiation which is reflected from the layers; in an event that the foci are not formed at an expected depth, or exhibit rapid spatial change as the seal 50 is moved past the measuring apparatus 200, an indication of air bubble occlusion or debris present in the seal 50 can be determined by processing detected signals generated by the optical receiver 666 in computing hardware 160, and thus a measure of quality of the seal 50. In FIG. 8D, one or more polarizing elements 674 are employed in one or more of the lens arrangements 670, 672; such polarizing elements can be implemented as microfabricated microgratings or polarizing plastics materials.

In an event that the packages 20 are fabricated from optically transparent plastics base layer (610) and cover layer (620) materials which have essentially same refractive index, for example 1.5, which is substantially different to that of air, namely 1.0 which can potentially be within the seal 50 as well as outside the seal 50, a prominent reflection occurs at interfaces between the layers 610, 620 and also between the layers 610, 600 due to substantial difference of the refractive indices. However, when the base layer (610) and the cover layer (620) are mutually bonded together to form a hermetically or antiseptically tight seal, reflection of radiation at interfaces present at seal will be less reflective. For reference, Fresnel reflection coefficient is defined by Equation 1 (Eq. 1):

$$R = \frac{n_2 - n_1}{n_2 - n_1} \qquad \text{Eq. 1}$$

wherein
R=Fresnel coefficient;
$n_1$=refractive index of a first optically transmissive medium; and
$n_2$=refractive index of a second optically transmissive medium.

Equation 1 (Eq. 1) defines that an optical boundary reflects more light if the relative refractive index, i.e. the difference in refractive index of the layers forming the optical boundary is as great as possible.

Figure 9:
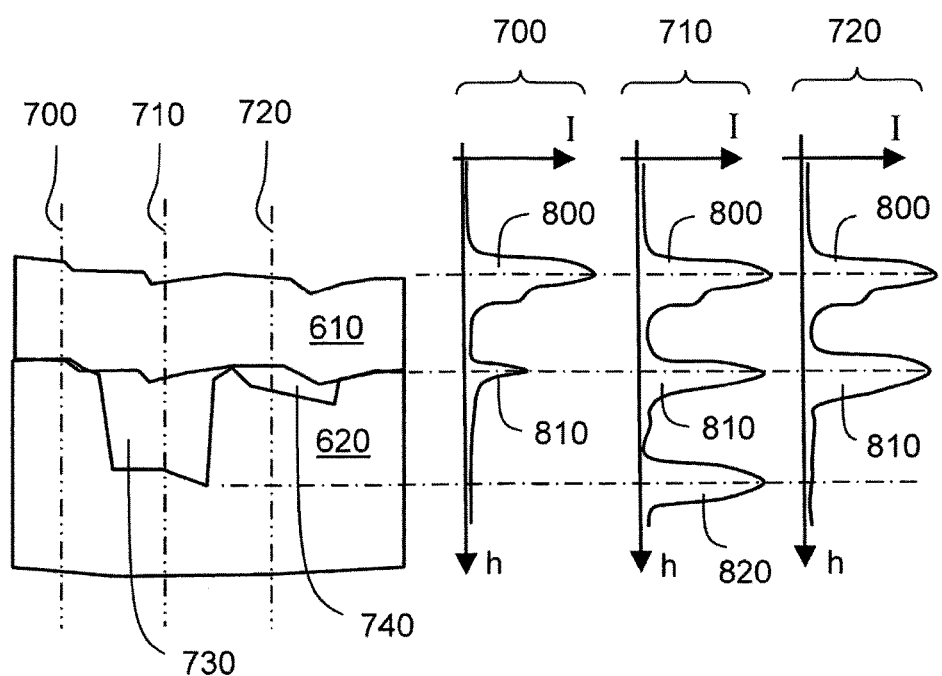
FIG. 9 is an illustration of reflected radiation signals received from a seal when interrogated using a measuring apparatus pursuant to the present invention.

For example, referring next to FIG. 9, example signals generated by the measuring apparatus 200 when interrogating the seal 50 are shown for first, second and third lateral measurement positions, namely 700, 710, 720 respectively. At the first lateral measurement position 700, the seal 50 is correctly formed, namely the layers 610, 620 are mutually bonded together. At the second lateral measurement position 710, a large bubble 730 is present, causing a spatially localized separation of the layers 610, 620. At the third lateral position 720, a small bubble 740 is present, causing a small localized separation of the layers 610, 620. First, second and third measuring peaks 800, 810, 820 sensed by the measuring apparatus 200 are also shown in FIG. 9 for the lateral measuring positions 700, 710, 720.

For the first lateral measurement position 700, the first peak 800 corresponds to a reflection occurring at the interface between the first layer 610 and air 600 at first distance h1 from the top of the layer 610. For the second lateral measurement position 710, the second peak 810 corresponds to a reflection occurring at the interface between the first layer 610 and the large bubble 730 at a second distance h2 from the top of the layer 610; moreover, the third peak 820 corresponds to a reflection at an interface between the large bubble 730 and the lower, base layer 620 at a third distance h3 from the top of the cover layer 610. For the third lateral position 720, the third peak 820 is absent on account of a shallowness of the small bubble 740, but the reflection from an interface of upper, cover layer 610 and the small bubble 740 occurs substantially at the second distance h2, and additionally the interface of lower layer 620 and small bubble for example causing a slight wavelength broadening of the peak 810; in other words, the shallow bubble 740 causes the third peak 820 to be moved in position to be coincident with the second peak 810. The measuring apparatus 200 is operable, for each lateral measurement position 700, 710, 720, to determine one or more of the peaks 800, 810, 820, wherein the measurement apparatus 200 determines the positions of the peaks 800, 810, 820 and their measurement amplitude. From the positions of the peaks 800, 810, 820 and their amplitudes, computing hardware of the measuring apparatus 200 executing one or more software products is rapidly capable of identifying occurrences of defects in the seal 50, without having to perform complex image processing; beneficially, a ratio of relative amplitude of the peaks 800, 810, 820, and/or their absolute values, are compared to one or more reference thresholds is employed to determine whether or not the seam 50 is acceptable. As an alternative to employing computing hardware, dedicated digital hardware, for example implemented using application specific integrated circuits (ASICs) can be used to process information corresponding to the peaks 800, 810, 820. Rapid real-time continuous scanning of the seam 50 is feasible to achieve using the measuring apparatus 200.

Beneficially, the measuring apparatus 200 is mounted on a packaging line, for example for checking the seal 50 as packages 20 are moved continuously along a conveyor belt. In such an implementation, the measuring apparatus 200 optionally determines an amplitude $I_1$ of the first peak 800 and compares amplitudes $I_2$, $I_3$ of the second and third peaks 810, 820 respectively, namely according to Equation 2 (Eq. 2):

$$A(x) = \frac{(I_2 + I_3)}{(I_1)} \qquad \text{Eq. 2}$$

wherein
x=lateral position along the seal 50.

The measuring apparatus 200 beneficially computes an average value for A in Equation 2 (Eq. 2) pursuant to Equation 3 (Eq. 3) for a plurality of positions x:

$$B_{ave} = \frac{1}{N}\sum_{i=1}^{N} A_i \qquad \text{Eq. 3}$$

wherein
$B_{ave}$=average ratio of intensities for a plurality of i lateral positions.

The measuring apparatus 200 beneficially determines a difference between measured A(x) to $B_{ave}$; in an event that the difference exceeds a defined threshold value, the measuring apparatus 200 indicates a fault condition in respect of the seal 50. As aforementioned, the measuring apparatus 200 is employed to measure around the entire seal 50; alternatively, the measuring apparatus 200 only inspects a subportion of the seal 50 to save measuring time, for example when employed in high-throughput packaging installations. As aforementioned, the measuring apparatus 200 is optionally provided with a polarizer before its light detector to enhance contrast in the measuring peaks 800, 810, 820, thereby providing for more representative measurement regarding quality of the seal 50.

The measurement apparatus 200 is capable of capturing a 3-dimensional (3-D) tomographic image of the seal 50 on account of the wavelengths $\lambda_1, \lambda_2, \lambda_3$ being representative of depths of the layers 610, 620 and their surfaces as a function of lateral position X which can be measured within a Cartesian (x, y, z) frame of reference. An example of such a tomographic image is provided in FIG. 10.

Figure 10:
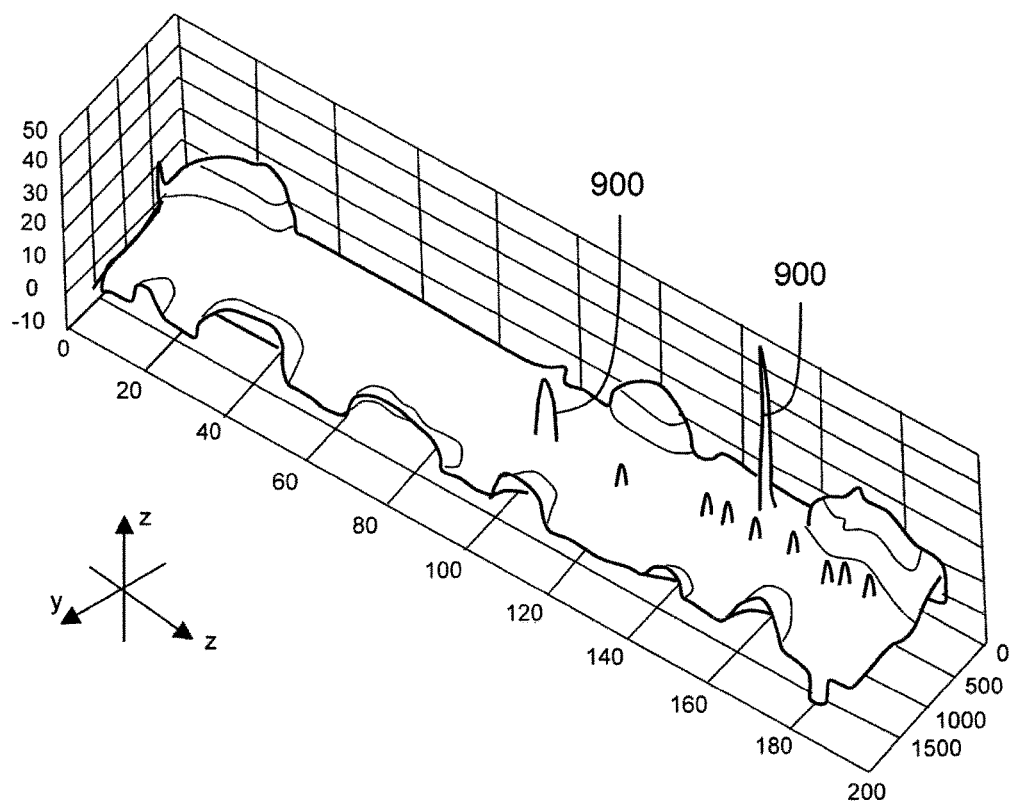
FIG. 10 is an illustration of a 3-dimensional (3-D) tomographic image of a seal as measured using measuring apparatus pursuant to the present invention.

Beneficially, when generating such a tomographic image as illustrated in FIG. 10, a matrix of, for example, 1000× 1000 pixels, are employed, wherein each pixel corresponds to a measurement location for the measuring apparatus 200. Other matrix sizes can be employed, for example 500×1000 pixels. In FIG. 10, air bubbles and/or debris formed or entrapped between the layers 610, 620 are represented by peaks, for example a peak 900.

The present invention is based a concept of employing a broad-band light source, for example a point source, an array of point sources, or a line source, exhibiting a wavelength spectrum s(λ) and a lens arrangement for focusing different wavelength components from the broad-band light source at different depths (h) within the seal 50. For example, in FIG. 8A, the optical source 660 is conveniently implemented as white-colour light emitting diode (LED), the beam splitter 662 is implemented using mirrors and/or prismatic components and/or an optical circulator. Moreover, the one or more optical components 664 are implemented using one or more lenses which are operable to exhibit axial colour aberration. The optical receiver 666 is conveniently implemented as a photodiode, a line sensor, a matrix sensor, a spectrograph or a hyperspectral imager.

Spectral content received at the optical receiver in FIG. 8A is expressed in the simplified form as Equation 4 (Eq. 4):

$$S_{detector}(\lambda)=S(\lambda_1)R(\lambda_1)g(\lambda-\lambda_1)+S(\lambda_2)R(\lambda_2)g(\lambda-\lambda_2) \quad \text{Eq. 4}$$

wherein
g(λ) is the peak form factor, for example a gaussian function, or a delta peak.

Thus, the apparatus 200 implemented as depicted in FIG. 8A generates on operation a first signal peak as given by Equation 5 (Eq. 5):

$$P_1(\lambda)=S(\lambda_1)R(\lambda_1)(\lambda-\lambda_1) \quad \text{Eq. 5}$$

and a second peak as given by Equation 6 (Eq. 6):

$$P_2(\lambda)=S(\lambda_2)R(\lambda_2)g(\lambda-\lambda_2) \quad \text{Eq. 6}$$

In the apparatus 200 of FIG. 8A, the detected signal $S_{detector}$ generated by the optical receiver 666 includes spectral information of the reflected radiation from the seal 50, namely wavelength and associated intensity, which is then quantitatively processed and the state of the seal 50 computed therefrom by analyzing resolved spectral points ($P_1, P_2, \ldots P_N$), wherein a parameter N is a number of resolved peaks. Optionally, the apparatus 200 is further operable to analyze further the state of the seal 50 by determining the relative the relative peak positions, the number of peaks, the relative peak intensities, and also the wavelength width of the peaks. Such detailed analysis performed in the computing hardware 160 is capable of providing a very detailed representation of a structure of the seal 50, for example in a manner as illustrated in FIG. 10 when the seal 50 is moved orthogonally in the apparatus 200.

When implementing the apparatus 200, using spectrograph-based detectors in its construction renders the apparatus 200 potentially expensive to manufacture; such spectrograph-based detectors exhibit a low signal-to-noise (S/N) ratio in operation and are often physically large in size. As aforementioned, it is desirable to employ an alternative type of detector, for example a single photodiode, a line sensor or a matrix sensor. Even when a simple sensor is employed in the apparatus 200, valuable information indicative of the state of the seal 50 can be obtained by analysing an intensity of the signal $S_{detector}$ which is then a sum as defined in Equation 7 (Eq. 7):

$$S_{detector}(\lambda)=S(\lambda_1)R(\lambda_2)(\lambda-\lambda_2)+S(\lambda_2)g(\lambda-\lambda_2)=P_1+P_2 \quad \text{Eq. 7}$$

As aforementioned, polarizing components are optionally included in the apparatus 200 to suppress the peak $P_1$ resulting in an uppermost region of the seal 50, namely at its ambient air-plastic interface; in such a scenario, the detected signals is then substantially P2 arising from an interface between the layers 610, 620.

Figure 3A:
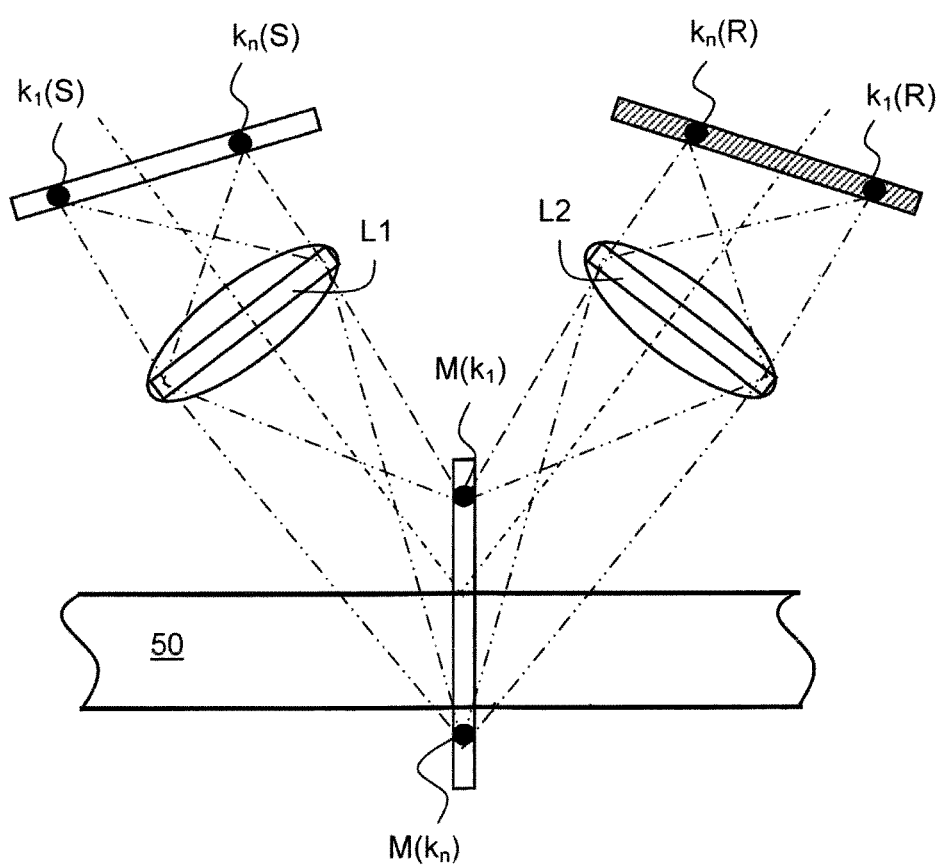
FIG. 3A and FIG. 3B are schematic illustrations of measuring apparatus pursuant to embodiments of the present invention.
Figure 3B:
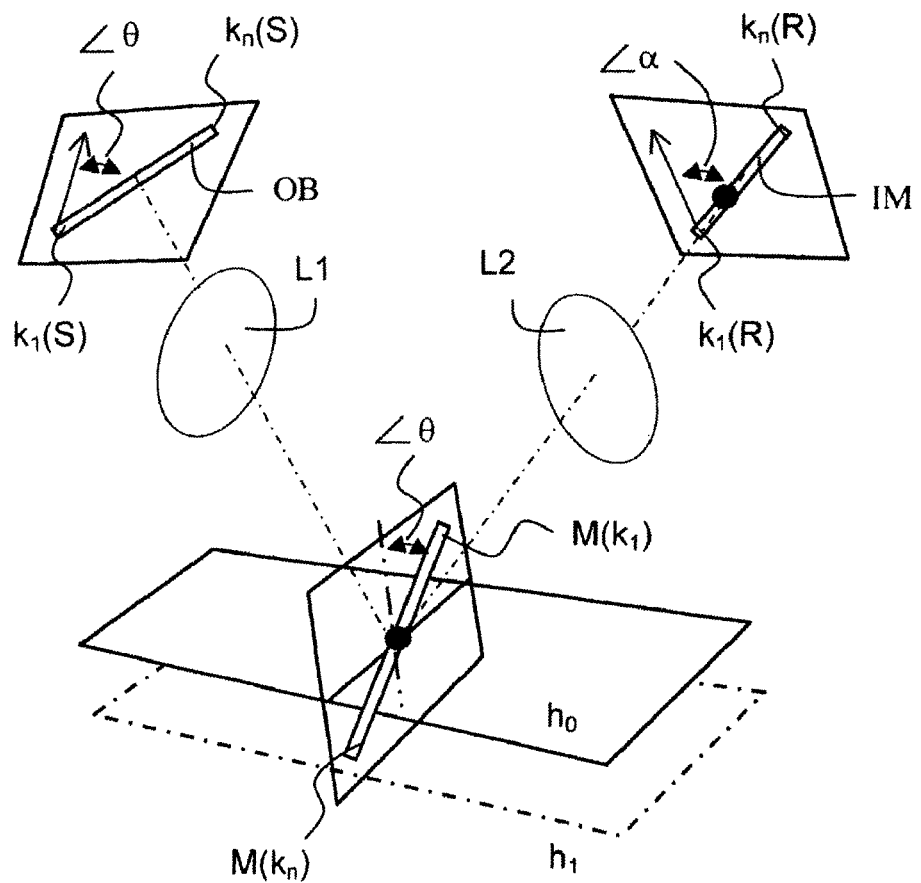
Figure 3B:
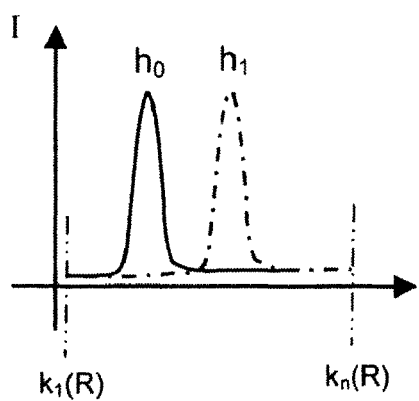

Referring next to FIG. 3A and FIG. 3B, there are illustrated an alternative embodiment of the present invention. In the measuring apparatus 200 implemented as in FIG. 3A and FIG. 3B, the illuminated sources ($k_1(S), k_2(S), \ldots k_n(S)$) are imaged to generate corresponding focal points ($M(k_1), M(k_2), \ldots M(k_n)$), for example implemented using confocal imaging techniques using a lens arrangement L1; for each point of the illumination source, a corresponding image point $k_1(R), k_2(R), \ldots k_n(R)$ is formed at the receiver as illustrated via a lens arrangement L2. In FIG. 3B, the detector, for example implemented as a multi-cell line detector, is optionally replaced with a single-cell detector, for example a PIN Silicon photodiode. Such a single-cell detector integrates all light received thereat, and generates a signal $S_{detector}$ which is lower in magnitude when there is only one reflecting surface present in the seal 50 being investigated, for example the top surface 220 at a depth $h_0$. When an additional reflecting surface is present within the seal 50 at a depth $h_1$ which also reflects light, the detector receives two strong peaks corresponding to depths $h_0$ and $h_1$ resulting in a large total integrated signal $S_{detector}$ from the single-cell detector. Accordingly, an additional reflecting surface present at substantially the depth $h_1$ results in the detected signal $S_{detector}$ being yet greater in magnitude. Such an arrangement enables a very fast and relatively inexpensive apparatus 200 to be provided for testing the seal 50. For this embodiment one option would be to use the wavelengths of the light (i.e. any light source can be used), however there are other alternative options since the measurement is based on detecting the focal points at different depths (h) in the steam. For example monochromatic light or close to monochromatic light can be used as illumination source.

Further in case of having continuous illumination source (($k_1(S), k_2(S), \ldots k_n(S)$), where n is infinite) the focal points (($M(k_1), M(k_2), \ldots M(k_n)$), where n is infinite) form a continuous line i.e. focal points are infinitesimally spaced apart. The corresponding image points ($k_1(R), k_2(R), \ldots k_n(R)$, where n is infinite) will form also a continuous line i.e. are infinitesimally spaced apart. In addition of arranging focal points as continuous line the focal points can be arranged as continuous area. The term "spatially spaced apart" can refer to two infinitesimally spaced points as well as points which are within measurable distance from each other.

Modifications to embodiments of the invention described in the foregoing are possible without departing from the scope of the invention as defined by the accompanying claims. Expressions such as "including", "comprising", "incorporating", "consisting of", "have", "is" used to describe and claim the present invention are intended to be construed in a non-exclusive manner, namely allowing for items, components or elements not explicitly described also to be present. Reference to the singular is also to be construed to relate to the plural. Numerals included within parentheses in the accompanying claims are intended to assist understanding of the claims and should not be construed in any way to limit subject matter claimed by these claims.

The invention claimed is:
1. A measuring apparatus (200) for inspecting interior portions of a seal (50) of an item (20), the item (20) comprising an optically transparent cover layer (620) and a base layer (610) and wherein the seal (50) is formed at an interface between the transparent cover layer (620) and the base layer (610), wherein the measuring apparatus (200) includes a radiation source (510, 520) for providing radiation for illuminating the base layer (610) through the cover layer (620) of the seal (50) of the item (20), and a detector (530, 540) for receiving radiation from the base layer (610) through the cover layer (620) of the item (20) for generating a corresponding detected signal,
wherein
- (a) the radiation source (510, 520) is arranged to focus the radiation through the cover layer (620) into a plurality of focal points at the seal (50) of the item (20), and wherein the focal points are mutually spatially spaced apart;
- (b) the detector (530, 540) is arranged to image one or more of the focal points and to be selectively sensitive to an intensity of radiation received from the one or more focal points to generate a detected signal; and
- (c) the measuring apparatus (200) is configured to receive the detected signal and process the detected signal to generate an output signal indicative of a state of the seal (50).

2. A measuring apparatus (200) as claimed in claim 1, wherein one or more focal points are generated in a direction which intersects a plane of the seal (50) when being inspected.

3. A measuring apparatus (200) as claimed in claim 1, wherein the radiation source (510, 520) employs chromatic dispersion occurring in one or more optical components for generating the plurality of focal points.

4. A measuring apparatus (200) as claimed in claim 1, wherein the focal points are generated as a function of depth (h) in a direction (700, 710, 720) which intersects the plane of the seal (50) when being inspected.

5. A measuring apparatus (200) as claimed in claim 1, wherein the detector (530, 540) includes a spectrometer (530) and an image camera (540) for generating the detected signal.

6. A measuring apparatus (200) as claimed in claim 1, wherein the detector (530, 540) includes one or more radiation polarizing elements (400) for increasing signal contrast in the detected signal arising from one or more defects being present in the seal (50).

7. A measuring apparatus (200) as claimed in claim 1, wherein the measuring apparatus (200) is configured to detect one or more radiation peaks (800, 810, 820) present in the detected signal as a function of depth (h) along interception of the seal to determine a magnitude of the one or more radiation peaks (800, 810, 820), and to determine from a relative ratio of the magnitude of the one or more radiation peaks (800, 810, 820) the state of the seal (50).

8. A measuring apparatus (200) as claimed in claim 7, wherein the determined state of the seal (50) includes at least one of: bubbles present at an interface of the seal (50), debris present at an interface of the seal (50).

9. A measuring apparatus (200) as claimed in claim 1, wherein the measuring apparatus (200) is configured to move the item (20) relative to the plurality of focal points, for enabling the measuring apparatus (200) to map a tomography of an interface between layers (610, 620) forming the seal (50) based on the relative refractive index of the layers.

10. A method of using a measuring apparatus (200) to inspect a seal (50) of an item (20), wherein the item (20) comprises a base layer (610) and an optically transparent cover layer (620) and wherein the seal (50) is formed at an interface between the base layer (610) and the cover layer (620), wherein the measuring apparatus (200) includes a radiation source (510, 520) for providing radiation for illuminating the seal (50) of the item (20) through the optically transparent cover layer (620), and a detector (530, 540) for receiving radiation reflected through the optically transparent cover layer (620) from the base layer (620) of item (20) for generating a corresponding detected signal, wherein the method includes the measuring apparatus (200):
- (a) focusing the radiation of the radiation source (510, 520) through the cover layer (620) into a plurality of focal points at the seal (50) of the item (20), wherein the focal points are mutually spatially spaced apart;
- (b) using the detector (530, 540) to image one or more of the focal points and to be selectively sensitive to an intensity of radiation received from the one or more focal points to generate a detected signal; and
- (c) receiving the detected signal and processing the detected signal to generate the output signal indicative of the state of the seal (50).

11. A method as claimed in claim 10, wherein the method includes employing in the radiation source (510, 520) chromatic dispersion occurring in one or more optical components for generating the plurality of focal points.

12. A method as claimed in claim 10, wherein the method includes generating the focal points as a function of either radiation wavelength ($\lambda$) and/or as a function of depth (h) in a direction which intersects a plane of the seal (50) when being inspected.

13. A method as claimed in claimed 10, wherein the method includes employing in the detector (530, 540) a spectrometer (530) and an image camera (540) for generating the detected signal.

14. A method as claimed in claim 10, wherein the method includes employing in the detector (530, 540) one or more radiation polarizing elements (400) for increasing signal contrast in the detected signal arising from one or more defects being present in the seal (50).

15. A method as claimed in claim 10, wherein the method includes the measuring apparatus (200) detecting one or more radiation peaks (800, 810, 820) present in the detected signal as a function of either radiation wavelength ($\lambda$) and/or as function of depth (h), to determine a magnitude of the one or more radiation peaks (800, 810, 820), and to determine from a relative ratio of the magnitude of the one or more radiation peaks (800, 810, 820) the state of the seal (50).

16. A method as claimed in claim 15, wherein the determined state of the seal (50) includes identifying at least one of: bubbles present at the interface of the seal (50), debris present at the interface of the seal (50).

17. A method as claimed in claim 10, wherein the method includes the measuring apparatus (200) moving the item (20) relative to the plurality of focal points, and mapping a tomography of the interface between the base layers (610) and the cover layer (620) forming the seal (50), wherein the base layers (610) and the cover layer (620) have mutually different refractive indices to the radiation received from the radiation source (510, 520).

18. A software product embodied on a non-transitory machine-readable data storage media, wherein the software product is executable upon computing hardware for executing a method as claimed in claim 10.

* * * * *